US005698400A

United States Patent [19]
Cotton et al.

[11] Patent Number: 5,698,400
[45] Date of Patent: Dec. 16, 1997

[54] DETECTION OF MUTATION BY RESOLVASE CLEAVAGE

[75] Inventors: Richard G. H. Cotton; Rima Youil, both of Melbourne, Australia; Borries W. Kemper, Köln, Germany

[73] Assignee: Avitech Diagnostics, Inc., Malvern, Pa.

[21] Appl. No.: 714,626

[22] Filed: Sep. 16, 1996

Related U.S. Application Data

[63] Continuation of Ser. No. 232,530, Apr. 25, 1994, abandoned.

[51] Int. Cl.$^6$ .............................. C12Q 1/68; C12Q 1/70; C12D 11/34; C07H 21/04
[52] U.S. Cl. .............................. 435/6; 435/5; 435/911; 435/912; 536/24.3; 536/24.31; 536/24.33
[58] Field of Search .............................. 435/6, 5, 91.1, 435/91.2; 536/22.1, 23.1, 24.3, 24.31, 24.32, 24.33

[56] References Cited

U.S. PATENT DOCUMENTS

| | | | |
|---|---|---|---|
| 4,683,202 | 7/1987 | Mullis | 435/91 |
| 5,217,863 | 6/1993 | Cotton et al. | |
| 5,459,039 | 10/1995 | Modrich et al. | 435/6 |

FOREIGN PATENT DOCUMENTS

| | | |
|---|---|---|
| WO 89/09835 | 10/1989 | WIPO. |
| WO 93/02216 | 2/1993 | WIPO. |

OTHER PUBLICATIONS

Jensch et al, (1989), "Cruciform cutting endonucleases from *Sacchromyces cerevisiae* and phage T4 show conserved reaction with branched DNAs" EMBO J. 8:4325–4334.

Galindez et al, (1991), "Characterization of genetic variation and 3'-azido-3' deoxythymidine resistance mutations of human immunodeficiency virus by RNase A mismatch cleavage method" Proc. Natl. Acad. Sci. 88:4280–4284.

Forrest et al, (1992), "Use of chemical cleavage of mismatch method for prenatal diagnosis of alpha-1-antitrypsin deficiency" Prenatal Diagnosis 12:133–137.

Winter et al, (1985), "A method to detect and characterize point mutations in transcribed genes: Amplification and overexpression of the mutant c-Ki-ras allele in human tumor cells" Proc. Natl. Acad. Sci. 82:7575–7579.

Beck et al, (Mar. 1993), "A denaturing gradient gel electrophoresis assay for sensitive detection of p53 mutations" Hum Genet 91:25–30.

Telenti et al, (Mar. 1993), "Detection of rifampicin-resistance mutations in Mycobacterium tuberculosis", Lancet 341:647–650.

Bhattacharyya et al.; Model for the Interaction of DNA Junctions and Resolving Enzymes; 1991 Academic Press Limited; 20:1191–17; 1991.

Youil, et al.; Poster Symposium –Session 40; The American Society of Human Genetics; 53:1257; 1993.

Cotton; Detection of Mutations in DNA; Current Biology Ltd; 3:24–30; 1992.

Cotton; Current Methods of Mutation Detection; Mutation Research; 285:125–144; 1993.

Dahl et al.; Pyruvate Dehydrogenase Deficiency Caused by Deletion of a 7–BP Repeat Sequence in the Ela Gene; Am. J. Hum. Genet.; 47:286–293; 1990.

DiLella et al.; Screening for Phenylketonuria Mutations by DNA Amplification with the Polymerase Chain Reaction; The Lancet; 497–499; Mar. 5, 1988.

Kemper et al.; Resolution of Holliday Structures by Endonuclease VII as Observed in Interactions with Cruciform DNA; Cold Spring Harbor Symp. Quant. Biol. 49:815–825, 1984.

Kleff et al.; Initiation of Heteroduplex–Loop Repair by T4–Encoded Endonuclease VII in Vitro; The EMBO Journal; 7:1527–1535; 1988.

Kosak et al.; Large–Scale Preparation of T4 Endonuclease VII from Over–Expressing Bacteria; Eur. J. Brochem.; 194:779–784; 1990.

Lilley et al.; Cruciform–Resolvase Interactions in Supercoiled DNA; Cell; 36:413–422; 1984.

Lin et al.; Geographical Clusters of Dengue Virus Type 2 Isolates Based on Analysis of Infected Cell RNA by The Chemical Cleavage at Mismatch Method; Journal of Virological Methods; 40:205–218; 1992.

Lu et al.; Detection of Single DNA Base Mutations with Mismatch Repair Enzymes; Genomics; 14:249–255; 1992.

Mizuuchi et al.; T4 Endonuclease VII Cleaves Holliday Structures; Cell; 29:357–365; 1982.

Mueller et al.; T4 Endonuclease VII Cleaves the Crossover Strands of Holliday Junction Analogs; Proc. Natl. Acad. Sci. USA; 85:9441–9445; 1988.

Muller et al.; Enzymatic Formation and Resolution of Holliday Junctions In Vitro; Cell; 60:329–336; 1990.

Parsons et al.; Resolution of Model Holliday Junctions by Yeast Endonuclease is Dependent Upon Homologous DNA Sequences; Cell; 52:621–629; 1988.

Parsons et al.; Interaction of a Four–Way Junction in DNA with T4 Endonuclease VII*; The Journal of Biological Chemistry; 265:9285–9289; 1990.

Pottmeyer et al.; T4 Endonuclease VII Resolves Cruciform DNA with Nick and Counter–Nick and Its Activity is Directed by Local Nucleotide Sequence; J. Mol. Biol.; 223:607–615; 1992.

Shenk et al.; Biochemical Method for Mapping Mutational Alterations in DNA with S1 Nuclease: The Location of Deletions and Temperature–Sensitive Mutations in Simian Virus 40*; Proc. Nat. Acad. Sci.; 72:989–993; 1975.

(List continued on next page.)

*Primary Examiner*—W. Gary Jones
*Assistant Examiner*—Jeffrey Fredman
*Attorney, Agent, or Firm*—Clark & Elbing LLP

[57] ABSTRACT

Methods are disclosed for detecting one or more mutations in an isolated test nucleic acid by forming a heteroduplex with a homologous control DNA and contacting the heteroduplex with a resolvase capable of recognizing at least one single base pair mismatch within the heteroduplex. In preferred embodiments of the invention, the resolvase is bacteriophage T4 endonuclease VII.

74 Claims, 4 Drawing Sheets

OTHER PUBLICATIONS

Smooker et al.; Identification and In Vitro Expression of Mutations Causing Dihydropteridine Reductase Deficiency; Biochemistry; 32:6443–6449; 1993.

Solaro et al.; Endonuclease VII of Phage T4 Triggers Mismatch Correction In Vitro; J. Mol. Biol., 230:868–877; 1993.

West; Enzymes and Molecular Mechanisms of Genetic Recombination; Annu. Rev. Biochem.; 61:603–40; 1992.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 1:

GCATCTTATC CTGTAGGAAA                                             20

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 2:

AGTACTGACC TCAAATAAGC                                             20

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CTGCTGTGGA ACTGGTGGAA        20

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 4:

ACAGGTAAGT GGCTCAGGTC        20

( 2 ) INFORMATION FOR SEQ ID NO: 5:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GCTCTTGAGC TATAAGTGG        19

( 2 ) INFORMATION FOR SEQ ID NO: 6:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GGGAGGTCGG GCTGCAGCA        19

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CTGCACAGCG GCCTGCTGAA        20

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CAGTTCAGGA CAAGGAGAGG        20

DETECTION OF MUTATION BY RESOLVASE CLEAVAGE

This is a continuation of application Ser. No. 08/232,530, filed Apr. 25, 1994, now abandoned.

BACKGROUND OF THE INVENTION

The ability to detect mutations in coding and non-coding DNA, as well as RNA, is important for the diagnosis of inherited disease. A gene mutation can be a single nucleotide change or multiple nucleotide changes in a DNA sequence encoding an essential protein. A single nucleotide change or multiple nucleotide changes can result in a frame shift, a stop codon, or a non-conservative amino acid substitution in a gene, each of which can independently render the encoded protein inactive. However, a gene mutation can be harmless, resulting in a protein product with no detectable change in function (i.e. a harmless gene polymorphism). Mutation in repetitive DNA can also lead to disease, as in, for example, human fragile-X syndrome, spinal and bulbar muscular dystrophy, and myotonic dystrophy.

A mutant nucleic acid which includes a single nucleotide change or multiple nucleotide changes will form one or more base pair mismatches after denaturation and subsequent annealing with the corresponding wild type and complementary nucleic acid. For example, G: A, C: T, C: C, G: G, A: A, T: T, C: A, and G: T represent the eight possible single base pair mismatches which can be found in a nucleic acid heteroduplex, wherein U is substituted for T when a nucleic acid strand is RNA. Nucleic acid loops can form when at least one strand of a heteroduplex includes a deletion, substitution, insertion, transposition, or inversion of DNA or RNA. Several screening methods have been designed to detect DNA mismatches in a heteroduplex. These methods include RNAse A digestion, chemical cleavage, as well as PCR- and primer extension-based detection methods (reviewed in Cotton, Curr. Opinion in Biotech. 3, 24 (1992)).

The resolvases (e.g. X-solvases of yeast and bacteriophage T4, Jensch et al. EMBO J. 8, 4325 (1989)) are nucleolytic enzymes capable of catalyzing the resolution of branched DNA intermediates (e.g., DNA cruciforms) which can involve hundreds of nucleotides. In general, these enzymes are active close to the site of DNA distortion (Bhattacharyya et al., J. Mol. Biol., 221, 1191, (1991)). T4 Endonuclease VII, the product of gene 49 of bacteriophage T4 (Kleff et al., The EMBO J. 7, 1527, (1988)) is a resolvase (West, Annu. Rev. Biochem. 61, 603, (1992)) which was first shown to resolve Holliday-structures (Mizuuchi et al., Cell 29, 357, (1982)). T4 Endonuclease VII has been shown to recognize DNA cruciforms (Bhattacharyya et al., supra; Mizuuchi et al., supra) and DNA loops (Kleff et al., supra), and it may be involved in patch repair. Bacteriophage T7 Endonuclease I has also been shown to recognize and cleave DNA cruciforms (West, Ann. Rev. Biochem. 61, 603, (1992) ). Eukaryotic resolvases, particularly from the yeast *Saccharomyces cerevisiae*, have been shown to recognize and cleave cruciform DNA (West, supra; Jensch, et al., EMBO J. 8, 4325 (1989)).

Other nucleases are known which recognize and cleave DNA mismatches. For example, S1 nuclease is capable of recognizing and cleaving DNA mismatches formed when a test DNA and a control DNA are annealed to form a heteroduplex (Shenk et al., Proc. Natl. Acad. Sci. 72, 989, (1975)). However, the rate of cleavage is unacceptably slow (Dodgson et al., Biochemistry 16, 2374, (1977)). The Mut Y repair protein of *E. coli* is also capable of detecting and cleaving DNA mismatches. However, the Mut Y repair protein is only capable of detecting 50% of the total number of mutations occurring in a mutant DNA segment (Lu et al., Genomics 14, 249, (1992)).

SUMMARY OF THE INVENTION

In general, the invention features a method for detecting one or more mutations in an isolated test nucleic acid which preferentially hybridizes to an isolated control DNA. The method includes:

a) denaturing, either independently or together, an isolated test nucleic acid and an isolated control DNA, wherein the denaturing is sufficient to form denatured test nucleic acid and denatured control DNA;

b) annealing the test nucleic acid to the control DNA, wherein the annealing is sufficient to form a heteroduplex between the test nucleic acid and the control DNA;

c) contacting the heteroduplex with a resolvase capable of recognizing at least a single base mismatch in the heteroduplex, the contacting being under conditions which permit the resolvase to cause one or more DNA breaks in the heteroduplex; and d) detecting the breaks as an indication of the presence of one or more mutations in the isolated test nucleic acid.

In preferred embodiments of this method, the resolvase is a bacteriophage resolvase, preferably either bacteriophage T4 Endonuclease VII or bacteriophage T7 Endonuclease I; or the resolvase is a eukaryotic resolvase, preferably a resolvase from the yeast *Saccharomyces cerevisiae*, more preferably any one of Endo X1, Endo X2 or Endo X3 resolvases from the yeast *Saccharomyces cerevisiae*.

In other preferred embodiments, the test nucleic acid and/or control DNA is derived from any one of a eukaryotic cell, eubacterial cell, a bacteriophage, a DNA virus, or an RNA virus. Preferred RNA viruses includes human T-cell leukemia virus and human immunodeficiency virus, preferably any one of HTLV-I, HTLV-II, HIV-1, or HIV-2. Preferred DNA viruses include any one of the family Adenoviridae, Papovaviridae, or Herpetoviridae.

In other preferred embodiments, the control DNA is isolated from an oncogene or a tumor suppressor gene of a eukaryotic cell, preferably a mammalian oncogene or a mammalian tumor suppressor gene. Preferably, the mammalian oncogene is any one of the abl, akt, crk, erb-A, erb-B, ets, fes/fps, fgr, fms, fos, jun, kit, mil/raf, mos, myb, myc, H-ras, K-ras, rel, ros, sea, sis, ski, src, or yes oncogenes and the tumor suppressor gene is any one of the p53, retinoblastoma, preferably RB1, adenomatous polyposis coli, NF-1, NF-2, MLH-1, MTS-1, MSH-2, or human non-polyposis genes.

In other preferred embodiments, the control DNA is isolated from any one of the β-globin, phenylalanine hydroxylase, $\alpha_1$-antitrypsin, 21-hydroxylase, pyruvate dehydrogenase E1α-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes genes of a eukaryotic cell.

In other preferred embodiments, the control DNA is a gene encoding a cell cycle control protein, preferably p21, p27, or p16.

In other preferred embodiments, the control DNA is isolated from a eubacterial cell, preferably of the order Spirochaetales, Kinetoplastida or Actinomycetales, more preferably of the family Treponemataceae, Trypanosomatidae, or Mycobacteriaceae, most preferably of the species *Mycobacterium tuberculosis*, *Treponema pallidum*, *Treponema pertenue*, *Borrelia burgdorferi*, or *Trypanosoma cruzi*.

In other preferred embodiments, the control DNA is a restriction enzyme fragment; the control DNA is produced by PCR amplification; the control DNA is produced by propagation in any one of a eukaryotic cell, a bacteriophage, a eubacterial cell, an insect virus, preferably a baculovirus derived vector, or an animal virus. Preferably the animal virus is a Simian Virus-40 or an adenovirus derived vector.

In a related aspect, the invention features a method wherein prior to step (c) above, the isolated control DNA and/or isolated test nucleic acid are tagged with at least one detection moiety, the detection moiety being a radioactive nucleotide, preferably $^{32}P$, $^{33}P$ or an $^{35}S$ labelled nucleotide; biotin; digoxygenin; a luminescent agent, preferably a fluorescent nucleotide, more preferably a fluorescein labelled nucleotide; a dye, preferably ethidium bromide, acridine orange, DAPI, a Hoechst dye; or an enzyme. Preferably the control DNA is tagged with a detection moiety only at a 5' end.

In another related aspect, the invention features a method wherein between step (c) and (d) above, the heteroduplex is tagged with at least one detection moiety; the detection moiety being a radioactive nucleotide, preferably $^{32}P$, $^{33}P$ or an $^{35}S$ labelled nucleotide; biotin; digoxigenin; a luminescent agent, preferably a fluorescent nucleotide, more preferably a fluorescein labelled nucleotide; a dye, preferably ethidium bromide, acridine orange, DAPI, a Hoechst dye; or an enzyme. Preferably, the heteroduplex is tagged with a detection moiety only at a 5' end.

In still another related aspect, the invention features a method wherein the heteroduplex is bound at a single 5' end to a solid support, preferably the solid support is an avidin-, or streptavidin-coated surface, a streptavidin-ferromagnetic bead, or a nylon membrane.

The invention also features a method for detecting one or more mutations in an isolated test DNA which preferably hybridizes to an isolated control DNA. The method includes:

a) denaturing, either independently or together, an isolated test DNA and an isolated control DNA, where the denaturing is sufficient to form a single-stranded test DNA and a single-stranded control DNA;

b) annealing the single-stranded test DNA to the single-stranded control DNA, the annealing being sufficient to form a heteroduplex between the single-stranded test DNA and the single-stranded control DNA;

c) contacting the heteroduplex with bacteriophage T4 Endonuclease VII under conditions which permit the endonuclease to recognize one or more DNA mismatches in the heteroduplex, preferably between one and seven (inclusive) DNA mismatches, and to cause one or more DNA breaks in the heteroduplex; and d) detecting the DNA breaks as an indication of the presence of one or more mutations in the isolated test DNA.

In preferred embodiments of this method, the test DNA and/or control DNA is derived from any one of a eukaryotic cell, eubacterial cell, a bacteriophage, a DNA virus, or an RNA virus. Preferred RNA viruses include human T-cell leukemia virus and human immunodeficiency virus, preferably any one of HTLV-I, HTLV-II, HIV-1, or HIV-2. Preferred DNA viruses include any one of the family Adenoviridae, Papovaviridae, or Herpetoviridae.

In other preferred embodiments, the control DNA is isolated from an oncogene or a tumor suppressor gene of a eukaryotic cell, preferably a mammalian oncogene or a mammalian tumor suppressor gene. Preferably, the mammalian oncogene is any one of the abl, akt, crk, erb-A, erb-B, ets, fes/fps, fgr, fms, fos, jun, kit, mil/raf, mos, myb, myc, H-ras, K-ras, rel, ros, sea, sis, ski, src, or yes oncogenes and the tumor suppressor gene is any one of the p53, retinoblastoma, preferably RB1, adenomatous polyposis coli, NF-1, NF-2, MLH-1, MTS-1, MSH-2, or human non-polyposis genes.

In other preferred embodiments, the control DNA is isolated from any one of the β-globin, phenylalanine hydroxylase, $\alpha_1$-antitrypsin, 21-hydroxylase, pyruvate dehydrogenase Elα-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes genes of a eukaryotic cell.

In other preferred embodiments, the control DNA is a gene encoding a cell cycle control protein, preferably p21, p27, or p16.

In other preferred embodiments, the control DNA is isolated from a eubacterial cell, preferably of the order Spirochaetales, Kinetoplastida or Actinomycetales, more preferably of the family Treponemataceae, Trypoanosomatidae, or Mycobacteriaceae, most preferably of the species *Mycobacterium tuberculosis*, *Treponema pallidum*, *Treponema pertenue*, *Borrelia burgdorferi*, or *Trypanosoma cruzi*.

In other preferred embodiments, the control DNA is a restriction enzyme fragment; the control DNA is produced by PCR amplification; the control DNA is produced by propagation in any one of a eukaryotic cell, a bacteriophage, a eubacterial cell, an insect virus, preferably a baculovirus derived vector, or an animal virus. Preferably the animal virus is a Simian Virus-40 or an adenovirus derived vector.

In a related aspect, the invention features a method where prior to step (c) above, the isolated control DNA and/or isolated test DNA are tagged with at least one detection moiety, the detection moiety being a radioactive nucleotide, preferably $^{32}P$, $^{33}P$ or an $^{35}S$ labelled nucleotide; biotin; digoxygenin; a luminescent agent, preferably a fluorescent nucleotide, more preferably a fluorescein labelled nucleotide; a dye, preferably ethidium bromide, acridine orange, DAPI, a Hoechst dye; or an enzyme. Preferably the control DNA is tagged with a detection moiety only at the 5' end.

In another related aspect, the invention features a method wherein between step (c) and (d) above, the heteroduplex is tagged with at least one detection moiety; the detection moiety being a radioactive nucleotide, preferably $^{32}P$, $^{33}P$ or an $^{35}S$ labelled nucleotide; biotin; digoxigenin; a luminescent agent, preferably a fluorescent nucleotide, more preferably a fluorescein labelled nucleotide; a dye, preferably ethidium bromide, acridine orange, DAPI, a Hoechst dye; or an enzyme. Preferably the heteroduplex is tagged with a detection moiety only at a 5' end.

Individuals skilled in the art will readily recognize that the compositions of the present invention can be assembled in a kit for the detection of mutations. Typically, such kits will include at least one resolvase capable of detecting a mutation. Preferably, the kit will include bacteriophage T4 Endonuclease VII in a suitable buffer and will optionally include isolated control DNA and pre-formed heteroduplexes with which to standardize reaction conditions.

The term "isolated nucleic acid," as used herein, refers to a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector. For example, DNA can be incorporated into bacteriophage, virus or plasmid vectors capable of autonomous replication. In addition, RNA can be converted into DNA by reverse transcriptase and subsequently incorporated into bacteriophage, virus or plasmid vectors capable of autonomous replication. The term "isolated nucleic acid" also includes a nucleic acid which exists as a separate molecule independent of other nucleic acids such as a nucleic acid fragment produced by chemical means or restriction endonuclease treatment.

"Homologous," as used herein in reference to nucleic acids, refers to the nucleotide sequence similarity between two nucleic acids. When a first nucleotide sequence is identical to a second nucleotide sequence, then the first and second nucleotide sequences are 100% homologous. The homology between any two nucleic acids is a direct function of the number of matching nucleotides at a given position in the sequence, e.g., if half of the total number of nucleotides in two nucleic acids are the same then they are 50% homologous. In the present invention, an isolated test nucleic acid and a control nucleic acid are at least 90% homologous. Preferably, an isolated test nucleic acid and a control nucleic acid are at least 95% homologous, more preferably at least 99% homologous.

A mutation, as used herein, refers to a nucleotide sequence change (i.e., a nucleotide substitution, deletion, or insertion) in an isolated nucleic acid. An isolated nucleic acid which bears a mutation has a nucleic acid sequence that is statistically different in sequence from a homologous nucleic acid isolated from a corresponding wild-type population. Examples of mutation bearing nucleic acid sequences which statistically differ in sequence from a homologous or a related nucleic acid isolated from a corresponding wild-type population have been reported (Balazs, L et al. Am. J. Hum. Genet. 44: 182 (1989); Sommer, S. S. et al. Mayo Clin. Proc. 64: 1361 (1989); Sommer, S. S. et al. BioTechniques, 12: 82 (1992); Caskey, C. T. et al. Science 256, 784 (1992); and references cited therein). The methods of the invention are especially useful in detecting a mutation in an isolated test or control nucleic acid which contains between 1 and 50 nucleotide sequence changes (inclusive). Preferably, a mutation in an isolated test or control nucleic acid will contain between 1 and 10 nucleotide sequence changes (inclusive), more preferably between 1 and 7 nucleotide sequence changes (inclusive).

The term complementary, as used herein, means that two homologous nucleic acids, e.g., DNA or RNA, contain a series of consecutive nucleotides which are capable of forming base pairs to produce a region of double-strandedness. This region is referred to as a duplex. A duplex may be either a homoduplex or a heteroduplex that forms between nucleic acids because of the orientation of the nucleotides on the RNA or DNA strands; certain bases attract and bond to each other to form multiple Watson-Crick base pairs. Thus, adenine in one strand of DNA or RNA, pairs with thymine in an opposing complementary DNA strand, or with uracil in an opposing complementary RNA strand. Guanine in one strand of DNA or RNA, pairs with cytosine in an opposing complementary strand. By the term "heteroduplex" is meant a structure formed between two annealed, complementary, and homologous nucleic acid strands (e.g. an annealed isolated test and control nucleic acid) in which one or more nucleotides in the first strand is unable to appropriately base pair with the second opposing, complementary and homologous nucleic acid strand because of one or more mutations. Examples of different types of heteroduplexes include those which exhibit a point mutation (i.e. bubble), insertion or deletion mutation (i.e. bulge), each of which has been disclosed in Bhattacharya and Lilley, Nucl. Acids. Res. 17, 6821–6840 (1989).

The term "mismatch" means that a nucleotide in one strand of DNA or RNA does not or cannot pair through Watson-Crick base pairing and $\pi$-stacking interactions with a nucleotide in an opposing complementary DNA or RNA strand. Thus, adenine in one strand of DNA or RNA would form a mismatch with adenine in an opposing complementary DNA or RNA strand. A first nucleotide cannot pair with a second nucleotide in an opposing complementary DNA or RNA strand if the second nucleotide is absent (i.e. an unmatched nucleotide).

A control DNA, as used herein, is DNA having a nucleotide sequence that is statistically indistinguishable in sequence from homologous DNA obtained from a corresponding wild-type population. A control DNA is at least 20 nucleotides in length. Preferably, a control DNA is between 100 and 40,000 nucleotides in length, more preferably between 150 and 5000 nucleotides in length.

A test nucleic acid, as used herein, is DNA or RNA, each of which bears at least one mutation. A test nucleic acid statistically distinguishable in sequence from homologous DNA obtained from a corresponding wild-type population. A test nucleic acid is at least 20 nucleotides in length. Preferably, a test nucleic acid is between 100 and 40,000 nucleotides in length, more preferably between 150 and 5000 nucleotides in length.

The formation of a duplex is accomplished by annealing two homologous and complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially, or completely, complementary. Thus, the phrase "preferentially hybridize" as used herein, refers to a nucleic acid strand which anneals to and forms a stable duplex, either a homoduplex or a heteroduplex, under normal hybridization conditions with a second complementary and homologous nucleic acid strand, and which does not form a stable duplex with other nucleic acid molecules under the same normal hybridization conditions. "Normal hybridization or normal stringency conditions" are those hybridization or stringency conditions which are disclosed below.

Unless defined otherwise, all technical terms and scientific terms used herein have the same meaning as commonly understood by one of ordinary skill in the art to which this invention belongs. All publications mentioned herein are incorporated by reference. Examples of the preferred methods and materials will now be described. These examples are illustrative only and not intended to be limiting as those skilled in the art will understand that methods and materials similar or equivalent to those described herein can be used in the practice or testing of the present invention.

Other features and advantages of the invention will be apparent from the following detailed description, and from the claims.

DESCRIPTION OF THE PREFERRED EMBODIMENTS

Figure 1:
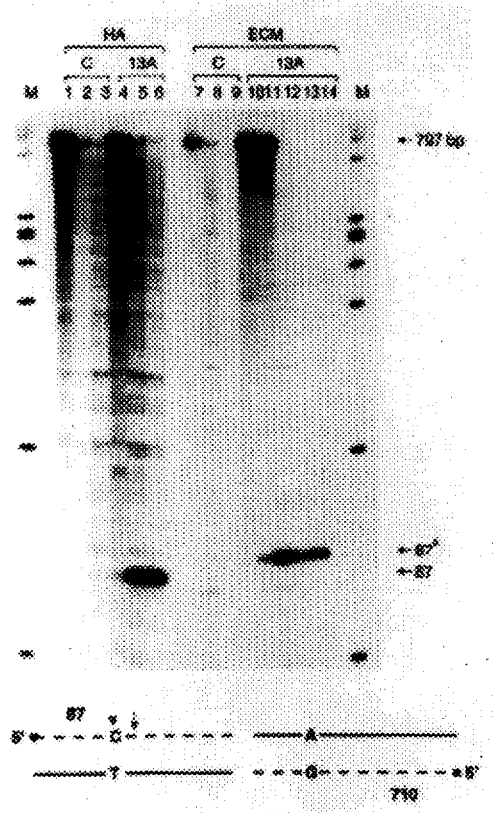
FIG. 1 represents an autoradiograph of CCM and EMC analysis of the PDH E1$\alpha$ gene (mutation 13A). This gene includes a C→A mutation 87 base pairs away from the 5' end of the fragment resulting in detectable mismatches.

We have found that bacteriophage T4 endonuclease VII, a resolvase which is known to cleave Holliday-structures as well as branched or looped DNA structures, is also capable of recognizing and cleaving heteroduplexes with a single nucleotide mismatch. This unexpected property of bacteriophage T4 endonuclease VII has allowed us to rapidly detect mutations in a test nucleic acid which includes at least one mutation. In general, the results indicate that resolvases, in particular, bacteriophage T4 endonuclease VII are useful for detecting mutations in a test nucleic acid, in particular, single base pair mutations.

I. Preparation of Bacteriophage T4 Endonuclease: T4 Endonuclease VII was prepared as described by Kosak and Kemper (Kosak et al., Eur. J. Biochem. 194, 779, (1990)). Stock solutions were maintained at 3,700 U/μl. The T4 Endonuclease VII reaction buffer used in the assay was prepared as a 10× concentrate as previously described (Kosak et al., supra). The heteroduplex annealing buffer was prepared as a 2× concentrate as previously described (Cotton, Methods in Molecular Biology 9, 39, (1991)). Conditions for 5'-end labelling DNA with polynucleotide kinase and general methods for performing denaturing polyacrylamide gel electrophoresis have been described (Sambrook et al., Molecular Cloning, A Laboratory Manual. 2nd Ed. Cold Spring Harbor Laboratory Press, (1989)).

II. Preparation of Control and Test DNA: Control and test DNA was prepared by PCR amplification (for a review on PCR see Ausubel, F. M. Current Protocols in Molecular Biology, Chapter 15, Greene Publishing Associates, Inc. and John Wiley & Sons, Inc (1993)). In these experiments, we were interested in detecting mutations in human genomic DNA (e.g. β-globin, phenylalanine hydroxylase (i.e. PAH) and α₁-antitrypsin human genomic DNA), plasmid DNA (e.g. a human 21-hydroxylase gene plasmid and a mouse mottled Menkes gene plasmid DNA), or cDNA (e.g. human pyruvate dehydrogenase-Elα subunit (i.e. PDH Elα) human dihydropteridine reductase (i.e. DHPR) cDNA, and human rhodopsin cDNA).

i) PAH gene: The PAH gene mutations IVS12 ntl and R408W were each individually PCR amplified using primers A and B as previously described (DiLella et al., Lancet 1, 497, (1988)). Exon 2 of the PAH gene was PCR amplified using the primers 5'-GCA TCT TAT CCT GTA GGAAA-3' (SEQ ID NO: 1) and 5'-AGT ACT GAC CTC AAA TAA GC-3' (SEQ ID NO: 2). The PCR conditions were 105 s at 95° C., 150 s at 58° C. and 3 min at 72° C. for 35 cycles.

ii) 21-hydroxylase gene: A 340 bp fragment of the normal (i.e., wild-type) and mutant 21-hydroxylase B gene were each individually amplified using the primers 5'-CTG CTG TGG AAC TGG TGG AA-3' (SEQ ID NO: 3) and 5'-ACA GGT AAG TGG CTC AGG TC-3' (SEQ ID NO: 4). A 178 bp section of the normal and mutant 21-hydroxylase B gene were each individually amplified using the primers 5'-GCT CTT GAG CTA TAA GTG G-3' (SEQ ID NO: 5) and 5'-GGG AGG TCG GGC TGC AGC A-3' (SEQ ID NO: 6). The normal 21-hydroxylase B gene and the 21-hydroxylase A gene were each amplified using the primers 5'-CTG CAC AGC GGC CTG CTG AA-3' (SEQ ID NO: 7) and 5'-CAG TTC AGG ACA AGG AGA GG-3' (SEQ ID NO: 8). PCR conditions for amplification of the 21-hydroxylase A and normal or mutant B gene fragments was 105 s at 95° C., 150 s at 62° C. and 3 min at 72° C. The DNA sequence of the A and B genes, as well as mutant alleles thereof can be found in Rodriques et al. (EMBO J. 6, 1653–1661 (1987)) and Cotton et al. supra.

iii) Other genes: PCR amplification of the β-globin, α₁-antitrypsin, and PDH Elα genes have been disclosed. For example, β-globin gene mutations (-87 (C→T), frameshift codon 6 (-A), nonsense codon 39 (C→T) and sickle mutation codon 6 (A→T) were each amplified using primers a and b, the IVS II-745 mutation was amplified using primers c and d as previously described (Dianzani et al., Genomics 11, 48, (1991)). The α₁-antitrypsin gene was amplified as described (Forrest et al., Prenatal Diagnosis 12, 133, (1992)). The PDH Elα gene (PDH gene mutations 13A, 18A and 31A) were amplified using primers PDH-P and PDH-E as previously described (Dahl et al., Am. J. Hum. Genet. 47, 286, (1990)). The DHPR gene was amplified using the primers GD and F as previously described (Smooker et al., Biochemistry 32, 6443, (1990)). The mouse mottled menkes gene (MMK) was amplified as described previously. The rhodopsin gene (mutation 83 (Asp→Ser in codon 15) was amplified as previously described (Sullivan et al., Arch. Ophthalmol. 111, 1512, (1993)).

A) Purification of PCR Products: PCR amplification products were purified by agarose (1.5%) gel electrophoresis, electroeluted onto Whatman I paper and then eluted with 1× TE (pH 8.0). In all experiments, a control DNA was 5' end-labelled with [gamma- ³²P] using T4 polynucleotide kinase (Boehringer-Mannheim). Following kinase treatment, the labelled control DNA was ethanol precipitated and the pellet washed three times with 70% ethanol to remove unincorporated label. The washed DNA pellet was resuspended in distilled water to give approximately 5 ng 5' end-labelled DNA/μl.

Figure 6:
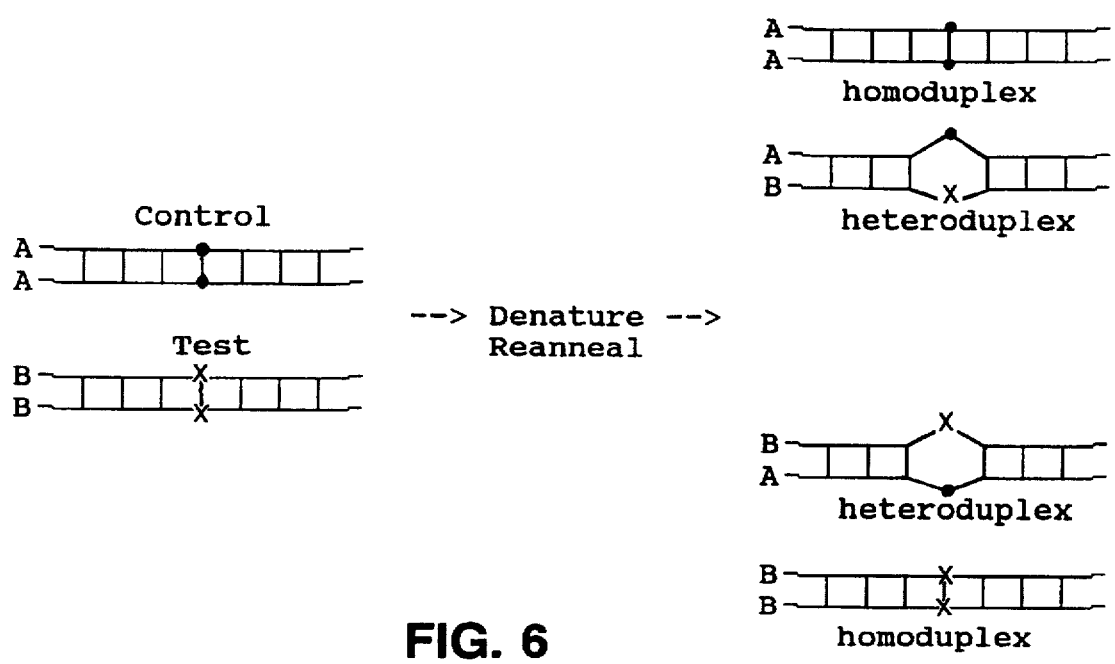
FIG. 6 is a schematic drawing illustrating how two heteroduplexes and two homoduplexes can arise from the denaturation and annealing of an isolated test nucleic acid (A) and a control DNA (B). The particular test nucleic acid shown includes one nucleotide mismatch. The bacteriophage T4 Endonuclease VII recognizes and cleaves single-base pair mismatches in each heteroduplex.

III. Formation of Control: Test DNA Heteroduplexes:
i) General Method: Single-stranded DNA was prepared by denaturing double-stranded test DNA and double-stranded control DNA with heat (i.e. between 90° C. and 100° C. inclusive). Alternatively, denaturation can be accomplished at lower temperatures by well-known modifications, for example, by adding glycerol to the denaturation buffer. As is shown in FIG. 6, after renaturation (see below), four double-stranded duplexes can be formed. We have found that bacteriophage T4 endonuclease VII is capable of cleaving a single base pair mismatch in each heteroduplex shown above, whereas, in general, homoduplexes are not cleaved. Therefore, because each heteroduplex is cleaved by bacteriophage T4 endonuclease VII, one or more mismatches in a heteroduplex can be readily detected. Similarly, unmatched base pairs are also detected in a heteroduplex with this method.

Those skilled in the art will appreciate that denaturation can also be conveniently accomplished by alkali denaturation, followed by renaturation in neutralizing buffer. Furthermore, when a test nucleic acid is RNA, preferably mRNA, heat denaturation will serve to produce RNA free of intrastrand nucleotide base pairing, thereby rendering the denatured test RNA a superior template for heteroduplex formation (see Sambrook et al. supra). In another alternative method, control and test nucleic acids can be denatured independently, either by heat or alkali, and mixed together in order to form heteroduplexes.

ii) Heteroduplex Formation: Heteroduplex formation between control and test DNA was performed in 50 μl (total volume) containing 1× annealing buffer as previously described (Cotton, supra) except that the annealing temperature was at 65° C. for 1 hour followed by 20 min at room temperature. Calculations of DNA concentration were based on 50–60 ng unlabelled DNA (10X excess) and 5 ng of 5' end-labelled DNA per single reaction. Heteroduplexes were prepared in 'bulk' in 50 μl volume and the pellet resuspended in the appropriate volume of distilled water. For example, if six reactions were required then 300 ng mutant DNA and 30 ng of labelled wild type DNA was used. After heteroduplex formation, the pellet was resuspended in 30 μl distilled water (i.e. 5 μl distilled water is taken per single reaction).

Homoduplexes were prepared in order to determine whether bacteriophage endonuclease VII can non-specifically cleave homoduplexes. An identical procedure was performed in order to prepare labelled homoduplex DNA except that an excess amount of unlabelled control DNA was annealed with labelled control DNA.

IV. Enzyme Mismatch Cleavage Assay (i.e. EMC)

5 μl of a labelled homoduplex DNA or a heteroduplex DNA (50–60 ng) was each added individually to 39 μl of distilled water and 5 μl 10× reaction buffer. Each sample was kept on ice. A cleavage reaction was initiated by the addition of 1 μl of the Bacteriophage T4 Endonuclease VII (100–3,000 U/μl as specified). A stock solution of the endonuclease was diluted to the required activity in the Bacteriophage T4 Endonuclease T4 dilution buffer. After addition of the resolvase, the tubes were spun briefly and incubated at 37° C. for 1 hour unless otherwise specified. Gel electrophoresis control samples were set up in which no bacteriophage T4 Endonuclease was added; the endonuclease being replaced with 1 μl of dilution buffer and incubated at 37° C. for 1 hour. After incubation, each sample was ethanol precipitated, washed in 70% ethanol, dried briefly and thoroughly resuspended by vortexing in 5 μl formamide urea loading dye. The 5 μl samples were heated to 100° C. and immediately loaded onto an 8% urea formamide acrylamide sequencing gel. Cleavage products were visualized by autoradiography and the sizes of the products were compared with radiolabelled ΘX174 HaeIII size marker. For a discussion on analyzing a nucleic acid sample by denaturing polyacrylamide gel electrophoresis see Sambrook et al. *Molecular Cloning: A Laboratory Approach*, Chapter 6 (1989).

V. Post-Digestion 5' End-Labelling of Heteroduplexes:

5' end-labelling of all four original 5' ends of each of the formed duplexes was performed after bacteriophage T4 endonuclease cleavage. The sensitivity of the EMC technique was increased by labelling these new 5' ends. The post digestion 5' end-labelling method was developed to screen kilobase lengths of DNA in the most time and cost effective manner.

Heteroduplexes were prepared in a 1:1 ratio of unlabelled control and unlabelled test DNA. The conditions used for heteroduplex formation were identical to those described above except that 25 ng of each of the DNA samples was used per reaction. The resolvase digestion was performed on 50 ng of unlabelled heteroduplex DNA and the products of digestion were 5' end-labelled in a total of 10 μl of (1× kinase buffer), 2 units of 5' polynucleotide kinase and 1 μl of a $\frac{1}{10}$ dilution of fresh [gamma-$^{32}$P] ATP. Following incubation for 45 min at 37° C., the sample was denatured at 70° C. for 10 min and the reaction mixture was ethanol precipitated. The pellet was washed 3 times in 70% ethanol, dried briefly, resuspended in 5 μl formamide-urea loading dye, and analyzed on a denaturing polyacrylamide gel as described above.

For simple and practical use found forming duplexes between equimolar mutant and wild type DNA, cleaving and then 5' end-labelling all 5' termini before polyacrylamide gel electrophoresis a useful modification. Post-digestion 5' end-labelling allows analysis of each strand for endonuclease induced breaks without the need to produce radiolabelled probes, thus maximizing the opportunity to detect mutations in a test DNA. When using the post-digestion 5' end-labelling method, two cleaved bands were always observed which reflected labelling of the cleavage products on both the control and test strands.

Those skilled in the art will appreciate that in each pre- and post-digestion 5' end-labelling method described above, a homoduplex consisting of either test DNA or control DNA is digested with bacteriophage T4 endonuclease VII in order to test for non-specific cleavage.

VI. Chemical Cleavage of Mismatch (CCM)

Chemical cleavage of heteroduplexes was used to verify that heteroduplexes had completely formed. CCM using osmium tetroxide and hydroxylamine was performed as previously described (Cotton, supra).

VII. Detection of DNA Mismatches Using Bacteriophage T4 Endonuclease VII

All four types of single base pair mismatch combinations which formed as a result of heteroduplex formation between different test and control DNAs were detected in these experiments. DNA mismatch combinations are organized by type and are summarized in Table 1 below:

TABLE 1

| | Mutational Change | Sets of Mismatches Produced |
|---|---|---|
| Type 1: | G <–> T or | G.A |
| | A <–> C | T.C |
| Type 2: | G <–> A or | G.T |
| | T <–> C | A.C |
| Type 3: | G <–> C | C.C |
| | | G.G |
| Type 4: | A <–> T | T.T |
| | | A.A |

FIG. 6 schematically describes how a single mutation in a test DNA has four chances of being detected in each of the two heteroduplexes formed in these experiments. Each heteroduplex includes two mismatched DNA strands which can be cleaved by a resolvase, preferably bacteriophage T4 Endonuclease VII. To be effective in detecting mutations at least one strand in the pair of mismatches of each set must be cleaved. In most cases, excess unlabelled test DNA was used and thus only cleavage of DNA strands containing the two mismatched bases present in the labelled probe were assayed. Experimental results are summarized in Table 2 below:

TABLE 2

Summary of the Mutations tested for by EMC as detailed in the text.

Figure 2:
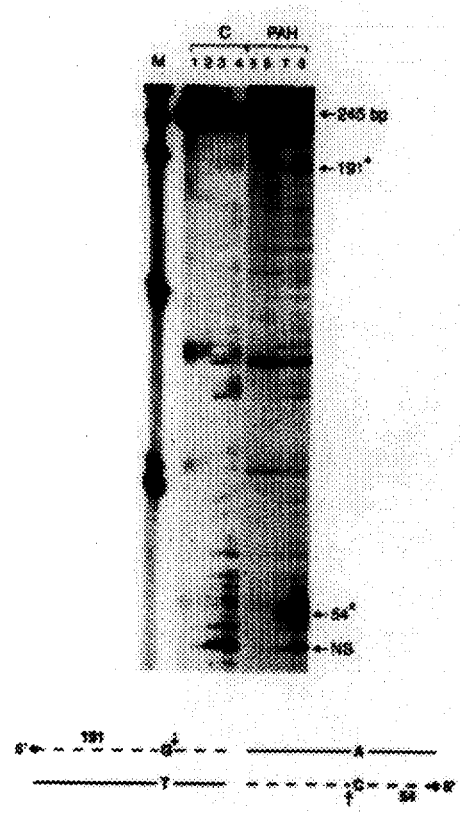
FIG. 2 represents an autoradiograph of EMC analysis of the PAH gene (mutation IVS 12NT1) containing a homozygous G→A mutation 191 base pairs from the 5' end of the PCR fragment resulting in detectable mismatches.
Figure 3A:
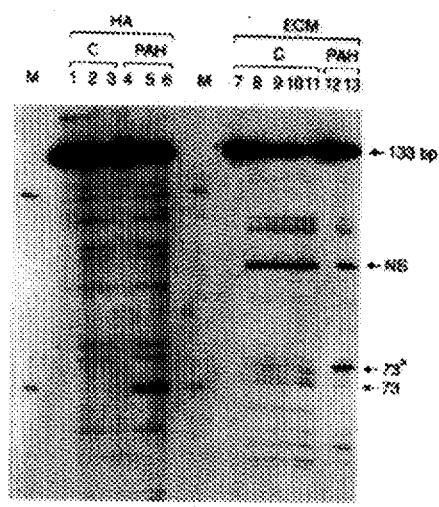
FIG. 3A represents an autoradiograph of CCM and EMC analysis of the PAH gene including a C→G mutation in exon 2. The mutation 73 base pairs from the 5' end of the fragment results in detectable mismatches.
Figure 3A:
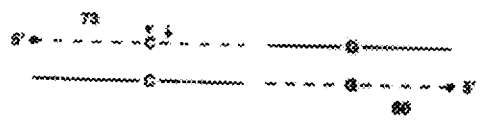
Figure 3B:
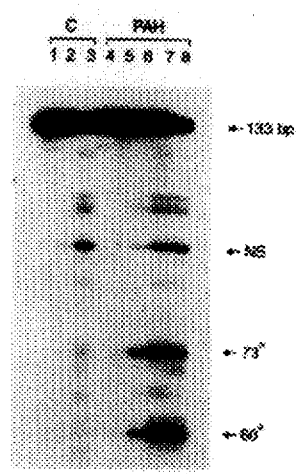
FIG. 3B represents an autoradiograph of post-digestion 5'-end labelling of the PAH gene (same fragment as in panel A) including a C→G mutation in exon 2. The mutation results in detectable mismatches.
Figure 3B:
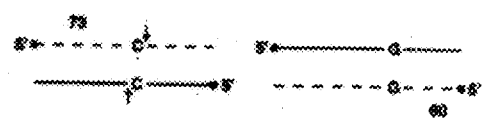
Figure 4:
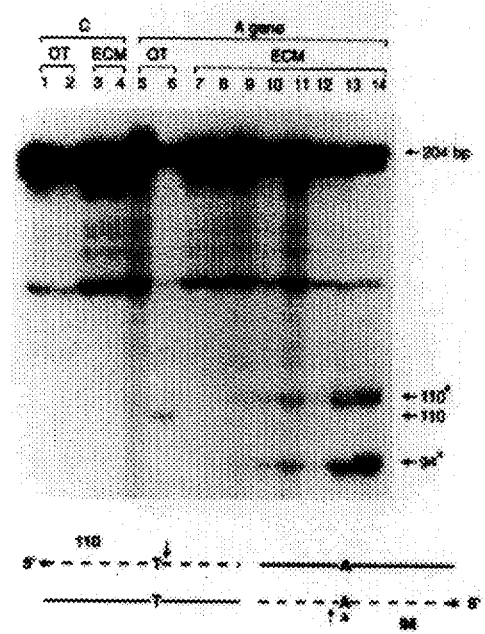
FIG. 4 represents an autoradiograph of CCM and EMC analysis of the 21-hydroxylase A gene (mutation A64) containing a T→A mutation at base pair 1004 of the gene. The mutation 110 base pairs from the 5' end of the fragment results in detectable mismatches.
Figure 5:
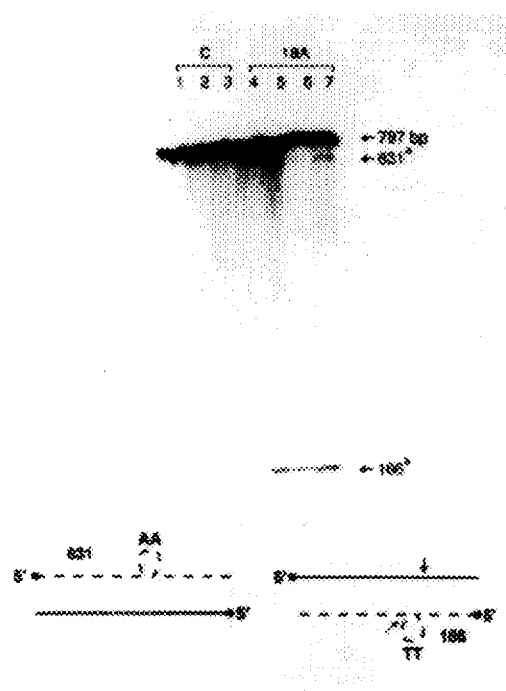
FIG. 5 is an autoradiograph of post-digestion 5'end-labelling of the PSH Elα gene (mutation 18A (K387 FS)) containing a homozygous -AA deletion 631 base pairs away from the 5' end of the section of the gene studied. The mutation results in detectable mismatches.

| Gene | Source[a] | Mutation | Total Fragment Length (bp) | Mismatch Set | Mismatch Detected | Non-specific Cleavage |
|---|---|---|---|---|---|---|
| $\alpha_1$-antitrypsin | Genomic (Hom) | G → A | 220 | G.T/C.A | C.A | + |
| 21-hydroxylase B gene[†] (mutation B3 and B4) | Plasmid (Hom) | T → C[b] A → C | 340 | G.T/C.A A.G/T.C | A.G/T.C | – |
| 21-hydroxylase B gene (mutation B3) | Plasmid (Hom) | T → C[b] | 178 | G.T/C.A | G.T | – |
| PAH E1α 13A | cDNA (Hom) | C → A | 797 | A.G/T.C | C.T see FIG. 1 | – |
| PAH (IVS12nt1) | Genomic (Hom) | G → A[b] | 254 | G.T/C.A | G.T/C.A see FIG. 2 | + |
| PAH (IVS12nt1) | Genomic (Het) | G → A[b] | 254 | G.T/C.A | G.T/C.A | + |
| PAH (R408W Exon12) | Genomic (Het) | C → T[b] | 254 | G.T/C.A | G.T/C.A | + |
| PAH (Exon 2) | Genomic (Het) | C → G | 133 | C.C/G.G | C.C[p] see FIGS. 3A, 3B | + |
| β-globin (–87) | Genomic (Hom) | C → G | 627 | C.C/G.G | C.C | – |
| β-globin[†] | | | | | | |
| (IVS H-745) | Genomic (Het) | C → G | 1377 | C.C/G.G | C.C/G.G | – |
| (IVS H-16) | | [C → G] | | C.C/G.G | C.C | – |
| (IVS H-74) | | [G → T] | | A.G/T.C | A.G/C.T | – |
| (IVS H-81) | | [C → T] | | G.T/C.A | G.T/C.A | – |
| (IVS H-666) | | [T → C] | | G.T/C.A | G.T/C.A | – |
| β-globin (codon 39) | Genomic (Hom) | C → T | 627 | G.T/C.A | G.T | – |
| β-globin (Sickle) | Genomic (Het) | A → T | 627 | A.A/T.T | ND | – |
| 21-hydroxylase A gene (mutation A64) | Genomic (Hom) | T → A | 204 | A.A/T.T | A.A/T.T See FIG. 4 | – |
| rhodopsin gene (83) Asn 15→Ser | cDNA (Het) | A → G | 1300 | G.T/C.A | ? | – |
| DHPR[c] | cDNA (Het) | T → C | 779 | G.T/C.A | G.T | – |
| MMK gene[c] | plasmid (X-linked) | [A → G] | 1502 | G.T/C.A | ? | – |
| MMK gene[c] | plasmid (X-linked) | [C → T] | 1502 | C.T/C.A | ? | – |
| MMK gene[c] | plasmid (X-linked) | [del 33 bp] | 1502 | 33 bp loops | ? | – |
| PDH E1α18A | cDNA (Hom) | del AA | 797 | TT/AA loops | TT loopp See FIG. 5 | – |
| PDH E1α31A | cDNA (Hom) | del 7 bp | 797 | 7 bp loops | ? | – |
| β-globin (Codon 6) | Genomic (Het) | del A | 797 | A/T loops | ND | – |

[a]Source of control and test DNA was either genomic, plasmid, or cDNA as described in the text. Test samples bear either homozygous (Hom) or heterozygous (Het) mutations.
[b]These mutations are in an identical fragment for their respective genes.
[c]These mutations were previously unknown.
[ ] These mutations are polymorphisms present in the wild-type population.
ND Mismatch was not detected by EMC.
? The actual mismatch cleaved by EMC could not be determined.
[†]More than one mismatch was detected in the fragment studied.
[p]Post digestion 5'-end labelling was performed on these fragments.
– Non-specific cleavage was not detected in these experiments Each mutation presented in Table 2 occurred only once in a test DNA unless otherwise specified. A detailed description of each experiment is disclosed below. These data describe the results of twelve type 1, three type 2, four type 3, two type 4 and four deletion mutations tested for cleavage with bacteriophage T4 Endonuclease VII:

i) Type 1 (Mismatch Set G.A/T.C)

The PAH E1α 13A gene includes a C→ A mutation 87 bp 3' to the 5' terminal end of the specific mutant gene studied (i.e. F205L). Using a 5' end-labelled control DNA as a probe, the resulting heteroduplexes contained C*.T and A.G* mismatches which could be detected with bacteriophage T4 endonuclease VII (FIG. 1). In FIG. 1, lanes 1, 2 and 3 are samples of control homoduplex DNA (i.e. lanes C) after incubation with hydroxylamine (i.e. lanes HA) for 0, 1 and 2 hrs. Lanes 4, 5 and 6 are samples of heteroduplex DNA including test DNA (i.e. lanes 13A) after incubation with hydroxylamine for 0, 1 and 2 hr, respectively. Lanes 7, 8 and 9 are samples of homoduplex DNA (i.e. lanes C) after incubation with 0, 1000 and 3000 units of T4 Endonuclease VII, respectively. Lanes 10–14 inclusive represent digestion of heteroduplex DNA including test DNA after incubation with 0, 250, 1000, 2000 and 3000 units of T4 Endonuclease VII, respectively. In lanes 5 and 6, a 87 bp fragment was observed on a denaturing acrylamide gel due to the fact that hydroxylamine is only capable of modifying a mismatched cytosine. With the EMC (lanes 10–14), a single band slightly larger than 87 bp fragment was observed indicating cleavage 3' of the C* in the C*.T mismatch.

In figures shown herein, a drawing beneath an autoradiograph is a schematic representation of the two types of heteroduplexes that were formed in each experiment. A broken line represents a control DNA strand and a straight line represents a test DNA strand. Arrows denote endonuclease cleavage sites on the end-labelled strand in each heteroduplex. A (*) represents a radioactively labelled nucleotide. A shaded triangle (▲) represents the actual cleavage site in a CCM reaction. A superscript ($^3$) refers to band sizes observed by EMC which were found to be larger than the expected band sizes determined by CCM. M denotes 5' end-labelled Hae III digested ΘX174 DNA.

ii) Type 2 (Mismatch Set G.T/A.C)

A 254 bp genomic DNA segment from the PAH gene of a patient homozygous for a G→A mutation (IVS12 (ntl)) was prepared by PCR-amplification. This particular PAH gene mutation occurs 191 bp 3' from the 5' end of the PCR amplified product (see FIG. 2). 5' end-labelled control DNA was annealed to unlabelled test DNA in order to form a heteroduplex. After cleavage with bacteriophage T4 endonuclease VII, two bands, one slightly large than 191 bp and another slightly larger than 54 bp band were observed (FIG. 2). In FIG. 2, lanes 1 to 4 inclusive are samples of control homoduplex DNA (i.e. lanes C) after incubation with 0, 250, 500 and 1000 units of T4 Endonuclease VII and lanes 5 to 8 inclusive are samples of heteroduplex DNA consisting of control and test DNA after incubation with 0, 250, 500 and 1000 units of T4 Endonuclease VII, respectively. These autoradiograms indicate DNA mismatches near a G* (G*.T mismatch) and C* (A.C* mismatch) respectively.

iii) Type 3 (Mismatch Set C.C/G.G)

Another mutant PAH gene segment was PCR amplified in order to form test DNA. This PAH mutant gene segment included a heterozygous C→G mutation at base 57 in Exon 2. This particular PAH mutation is 73 bp 3' from the 5' end of the 133 bp segment that was analyzed (see FIG. 3A). FIG. 3A is an autoradiograph of CCM and EMC analysis of this test PAH gene segment. Lanes 1, 2 and 3 are samples of control homoduplex DNA (i.e. lanes C) after incubation with hydroxylamine for 0, 1 and 1.5 hr. Lanes 4, 5 and 6 are samples of heteroduplex containing control and test DNA (i.e. lanes PAH) after incubation with hydroxylamine for 0, 1 and 1.5 hr, respectively. Lanes 7 to 11 inclusive are samples of control homoduplex after incubation with 0, 1000, 2000, 2500 and 3000 units of T4 Endonuclease VII. Lanes 12 and 13 are samples of PAH heteroduplex after incubation with 0 and 1000 units of T4 Endonuclease VII, respectively.

FIG. 3B is an autoradiograph of post-digestion 5' end-labelling (described below) of the PAH gene containing the same heterozygous C→G mutation in Exon 2. Lanes 1, 2 and 3 are samples of control homoduplex DNA (i.e. lanes C) after incubation with 0, 250 and 1000 units of T4 Endonuclease VII and lanes 4 to 8 inclusive are samples of heteroduplex containing control DNA and test DNA (i.e. PAH) after incubation with 0, 100, 250, 500 and 1000 units of T4 Endonuclease VII, respectively.

As can be seen in both FIGS. 3A and 3B, heteroduplex formation between 5' end-labelled control DNA and unlabelled test DNA produced C*.C and G.G* mismatches. CCM using hydroxylamine detected only the C*.C containing heteroduplex. For example, the 73 bp 5' end-labelled strand derived from the control DNA probe (in this case the sense strand) was observed on denaturing polyacrylamide gel electrophoresis. EMC of the same heteroduplex showed a related cleavage pattern, except that a band slightly larger than 73 bp fragment was also observed (FIG. 3A). This band results from cleavage near the C*.C heteroduplex.

Heteroduplex cleavage by T4 Endonuclease VII results in new nucleotide 3' OH and 5' PO$_4$ ends. 5'-end labelling involves only labelling the 5' OH ends of amplified DNA with [gamma-$^{32}$P] ATP using 5' T4 polynucleotide kinase. Hence any fragments 3' to a heteroduplex cleavage site will NOT be observed on autoradiography. However, post-digestion 5' end-labelling allowed detection of a 60 base pair fragment previously undetected in FIG. 3A. For example, post digestion 5'-end labelling of the heteroduplex analyzed in FIG. 3A, allowed detection of new bands slightly larger than 60 and 73 bp bands on the autoradiograph (see FIG. 3B). Taken together, comparison of FIGS. 3A and 3B showed that by adding a post-digestion 5'-end labelling step after bacteriophage T4 endonuclease VII cleavage, an extra cleavage due to the one mutation could be identified.

iv) Type 4 (Mismatch Set A.A/T.T)

A 204 bp segment of a mutant 21-hydroxylase A gene was PCR amplified from plasmid DNA (see above). The DNA segment contained a T→ A mutation at nucleotide 1004 of the 21-hydroxylase A gene. This mutation is 110 bp 3' from the 5' end of the gene segment. Annealing a single-stranded control DNA to a single-stranded test DNA resulted in a heteroduplex containing both A.A* and T*.T mismatches.

EMC with 5' end-labelled control DNA detected two bands on denaturing polyacrylamide gels; one slightly greater than 110 bp and the other slightly greater than 94 bp (FIG. 4). In FIG. 4, lanes 1 and 2 represent samples of control homoduplex DNA (i.e. lanes C) after incubation with osmium tetroxide (OT) for 0 and 5 min and lanes 3 and 4 represent samples of control homoduplex DNA after incubation with 0 and 250 units of T4 Endonuclease VII. Lanes 5 and 6 represent samples of heteroduplex DNA containing control and test DNA (i.e., 204 bp mutant 21-hydroxylase A gene segment) after incubation with OT for 0 and 5 minutes. Lanes 7 and 8 are samples of after incubation with 0 and 250 units of T4 Endonuclease VII, respectively. Lanes 9, 10 and 11 are samples of test DNA after incubation with 500 units of T4 Endonuclease VII for 1, 3 and 16 hr. Lanes 12, 13 and 14 are samples of test DNA after incubation with 1000 units of T4 Endonuclease VII for 1, 3 and 16 hr at 37°, respectively. These results confirm that bacteriophage T4 endonuclease VII is capable of recognizing both control DNA strands in a heteroduplex, each of which includes a DNA mismatch. CCM on this sample showed only a 110 bp fragment obtained after modification and cleavage of the mismatched T base in the sense strand of the probe.

iv) Type 5: DNA deletions forming a heteroduplex loop

PDH Elα18A is a 797 base pair fragment of a mutant PDH gene which includes a deletion of two deoxyadenosines 631 bp away from the 5' end of the gene segment. EMC detected a single band slightly greater than 166 bp signifying cleavage near the 'TT' loop only (data not shown). Post-digestion 5' end-labelling of the same segment showed two bands, one slightly greater than 166 bp produced by cleavage near the 'TT' loop and the other slightly greater than 631 bp produced by cleavage near the 'AA' position on the opposing strand (FIG. 5). In FIG. 5, lanes 1, 2 and 3 are samples of control homoduplex DNA (i.e. lanes C) after incubation with 0, 500 and 1000 units of T4 Endonuclease VII. Lanes 4 to 7 inclusive are samples of test heteroduplex containing control DNA and test DNA after incubation with 0, 500, 1000 and 2000 units of T4 Endonuclease VII, respectively.

It will be apparent to the art-skilled that the above-described methods of detecting mutations are not limited to bacteriophage T4 endonuclease VII detection methods described above. For example, several resolvases are disclosed below which are known to recognize and cleave DNA cruciforms. The above-described methods may be used to test these resolvases for the ability to detect mutations in an isolated test nucleic acid. In addition, the art-skilled will recognize that methods described above are not limited to any specific nucleic acid template, labelling method, or detection technique. Additional embodiments of the invention are set forth below:

i) Other resolvases: Bacteriophage endonuclease VII is one example of a resolvase known to cleave DNA cruciforms. Additional resolvases with similar activity include bacteriophage T7 endonuclease I, and the *S. cerevisiae* cruciform cleaving enzymes Endo X1, Endo X2, and Endo X3 (reviewed in West, S. C. supra). Methods for purifying bacteriophage T7 endonuclease I (deMassy, B., et al. J. Mol. Biol. 193: 359 (1987) ), Endo X1 (West, S. C. and Korner, A. PNAS, 82, 6445 (1985); West, S. C. et al. J. Biol. Chem. 262: 12752 (1987)), Endo X2 (Symington, L. S. and Kologner, R. PNAS 82: 7247 (1985)), Endo X3 (Jensch F. et al. EMBO J. 8, 4325 (1989)) have been disclosed. Preliminary studies have shown that Endo X3 is capable of detecting C.C mismatches in much the same way as bacteriophage T4 endonuclease VII, indicating that the yeast resolvases, like bacteriophage T4 endonuclease VII, are also capable of recognizing and cleaving near single base-pair mismatches in a heteroduplex. In order to examine the properties of bacteriophage T7 endonuclease I and the yeast resolvases in more detail, each enzyme can be purified by methods disclosed above. The ability of each purified resolvase to detect mutations may be examined by using the assays described herein.

ii) Additional DNA sequences: The above described methods show that bacteriophage T4 endonuclease VII is capable of detecting one or more base-pair mismatches in a heteroduplex. The art-skilled will recognize that these methods are not limited to any specific nucleic acid sequence disclosed herein. For example, a DNA restriction fragment of known or unknown DNA sequence which is suspected of bearing at least one DNA mutation, may be used as a test DNA in the formation of a heteroduplex. Preferably the DNA restriction fragment will be at least 20 base pairs in length. More preferably, the DNA restriction fragment will be between 50 and 40,000 base pairs in length inclusive, most preferably between 100 and 5000 base pairs in length inclusive. In experiments where particularly large DNA fragments are analyzed (i.e. larger than 2 kb) it will be desirable to cleave the fragment with a second restriction enzyme in order to obtain a fragment of a size suitable for denaturing polyacrylamide gel electrophoresis (<2 kb). The choice of a second restriction enzyme will guided by creating a restriction enzyme map of the restriction fragment.

In another example, a test DNA template suspected of harboring at least one DNA mutation and for which at least a partial DNA sequence is known can be used as a source of PCR-amplified test DNA. A DNA template must include: 1) a region suspected of harboring at least one DNA mutation and 2) include sufficient DNA flanking a suspected mutation to serve as a template for DNA oligonucleotide primer hybridization and PCR amplification. The PCR amplified region is the intervening region between the 3' ends of the two DNA oligonucleotide primers hybridized to the DNA template. This intervening region harbors at least one DNA mutation. As outlined above, PCR amplification is performed by first hybridizing two DNA oligonucleotide primers to a DNA template harboring at least one DNA mutation, then completing multiple rounds of PCR amplification; the PCR amplified DNA being used as test DNA for heteroduplex formation as described above. The design of the two DNA oligonucleotide primers used to amplify a DNA template and prepare test DNA are guided by the DNA sequence flanking a suspected mutation site and two important parameters: 1) DNA oligonucleotide primer size, and 2) the size of the intervening region between the 3' ends of the DNA oligonucleotide primers hybridized to a DNA template. Preferably, a DNA oligonucleotide primer will be at least 12 nucleotides in length. More preferably, a DNA oligonucleotide primer will be between 15 and 50 nucleotides in length inclusive, most preferably between 15 and 25 nucleotides in length inclusive. The size of the intervening region between the 3' ends of the two DNA oligonucleotides hybridized to a DNA template will be governed by 1) the well known size limitations of templates amplified by PCR, and 2) the resolving power of a particular gel (ie. polyacrylamide or agarose gel) used to detect resolvase cleavage sites (see below). In general, the intervening region between the 3' ends of the two DNA oligonucleotides hybridized to a DNA template will be at least 50 base pairs in length inclusive. Recent advances in PCR technology have allowed amplification of up to 40 kb of DNA. Preferably, the intervening region will be between 100 and 40,000 base pairs in length inclusive, more preferably between 150 and 5000 base pairs in length inclusive. Those skilled in the art will appreciate that where the flanking DNA sequence is only partially known, a degenerate DNA oligonucleotide primer may be used to prepare test DNA by PCR amplification.

In another example, template DNA suspected of harboring at least one DNA mutation can be subcloned into a suitable cloning vector and amplified using known DNA oligonucleotide primers which hybridize to the cloning vector and are adjacent to the insertion site of the DNA template. In this instance, no template DNA sequence information is required because the DNA oligonucleotide primers used for PCR amplification hybridize to a vector of known DNA sequence and not the inserted template DNA. For example, the Bluescript™ vector can be used to sub-clone a DNA template into an acceptor site according to the manufacturer's instructions (Stratagene Cloning Systems, La Jolla, Calif., Product Catalogue, (1992)). The T7 and T3 DNA primers of the Bluescript vector can be used to PCR amplify the inserted DNA template (or concomitantly to sequence the inserted DNA template). Other commercially available sub-cloning vectors may also be used. These include, without limitation, phage lambda based insertion vectors and other prokaryotic and eukaryotic vectors (i.e., bacteriophage, insect virus (baculovirus) or animal virus (SV-40 or adenovirus) based vectors described by Stratagene supra, and Sambrook et al. supra). As described above, the PCR amplified test DNA template can be used as a source of test DNA to make heteroduplexes for cleavage with a resolvase, preferably bacteriophage T4 endonuclease VII. In an alternative method, a vector which includes a DNA insert bearing at least one DNA mutation may be first amplified by propagation in bacteria, phage, insect or animal cells prior to PCR amplification (see Sambrook et al. supra). If sufficient DNA is available (i.e. at least 1 nanogram), the PCR amplification step can be eliminated.

In yet another example, RNA suspected of bearing at least one mutation may be purified from cells or tissues by techniques well-known in the art. For example, RNA may be optionally purified by olido-dT chromatography to prepare mRNA (see for example Sambrook et al. supra and Ausubel et al. supra). In cases where ribosomal RNA is the subject of analysis or a particular mRNA (e.g. collagen) is in abundance, oligo-dT chromatography will not be necessary. Purified RNA or mRNA will be heat denatured in order to ensure complete single-strandedness and hybridized with control DNA (i.e. a control cDNA) in order to form RNA:DNA heteroduplexes. A method for forming RNA: DNA duplexes are well known in the art and have been described in detail (see Sambrook et al. supra, pp. 7.62–7.65). After formation of an RNA: DNA heteroduplex, the EMC method described above can be used to detect mismatches produced by mispairing between the cDNA and the RNA. In preferred embodiments, the control DNA will be 5' end-labelled while the RNA will not be labelled. Alternatively, RNA can be uniformly labelled by adding radiolabelled uracil to living cells or tissues.

The invention is particularly useful for detecting single base pair mutations in cloned DNA, for example, those mutations introduced during experimental manipulation of the cloned DNA (e.g. transformation, mutagenesis, PCR amplification, or after prolonged storage or freeze: thaw cycles). As an example, a DNA segment can be used to form a heteroduplex; wherein the control DNA is DNA not subjected to experimental manipulation and the test DNA is DNA subjected to experimental manipulation. The methods described herein can be used as a quick and inexpensive screen to check for mutations in any cloned nucleic acid.

Those skilled in the art will appreciate that the present invention can also be used to type bacteria and viruses. By "type" is meant to characterize an isogeneic bacterial or viral strain by detecting one or more nucleic acid mutations that distinguishes the particular strain from other strains of the same or related bacteria or virus. For example, bacteria or viruses which share specific DNA mutations would be of similar type. As an example, genetic variation of the human immunodeficiency virus has led to the isolation of distinct HIV types, each bearing distinguishing gene mutations (Lopez-Galindez et al., PNAS 88, 4280 (1991)). Examples of test DNAs of particular interest for typing include test DNA isolated from viruses of the family Retroviridae, preferably the human T-lymphocyte viruses or human immunodeficiency virus, in particular any one of HTLV-I, HTLV-II, HIV-1, or HIV-2. Those art-skilled will appreciate that retroviral RNA can be reverse transcribed and conveniently subcloned in vaccinia virus vectors for the production of DNA (see Yammamoto et al. J. Immunol. 144, 1999; Nixon et al. Nature 33, 484 (1988); Hu, S-L. et al. WO 87/02038; and references therein). Other examples of test DNAs of interest for typing include DNA viruses of the family Adenoviridae, Papovaviridae, or Herpetoviridae,; as well as test DNA isolated from microorganisms that are pathogenic to mammals, preferably humans. Preferred microorganisms for typing include bacteria of the order Spirochaetales, preferably of the genus Treponema or Borrelia; the order Kinetoplastida; preferably of the species *Trypanosoma cruzi;* the order Actinomycetales, preferably of the family Mycobacteriaceae, more preferably of the species *Mycobacterium tuberculosis;* or the genus Streptococcus.

The invention is also useful for detecting mutations in repetitive DNA associated with a mammalian disease. For example, one or more mutations in repetitive DNA is associated with human fragile-X syndrome, spinal and bulbar muscular dystrophy, and myotonic dystrophy (Caskey, T. et al. supra). Repetitive DNA from each of these genes can serve as a test nucleic acid in the methods described herein.

iii) Additional labelling Techniques: The above-described methods disclose 5' end-labelling of DNA with radioactive phosphorous either before heteroduplex formation or after heteroduplex formation and cleavage (i.e. post-digestion 5' end-labelling). Those skilled in the art will appreciate that heteroduplexes can be tagged with one or more radioactive or non-radioactive detection moieties by a variety of methods. For example, during PCR amplification of DNA in order to obtain DNA for heteroduplex formation, one or more deoxyribonucleotides (i.e. dNTPs: dA, dG, dC or T) radiolabelled in the α position with radioactive phosphorus or sulfur (e.g. $^{32}P$, $^{33}P$, or $^{35}S$) can be added to the PCR amplification step in order to internally label test DNA. In general, 0.1–50 μCi of one or more radioactively labelled dNTPs can be added to a PCR reaction and excess label removed by Sephadex G-50 column chromatography (i.e., a spin column). Furthermore, 5' end-labelling of test DNA either before or after bacteriophage T4 endonuclease VII digestion may be accomplished by using radiolabelled deoxyribonucleotides. Alternatively, test DNA or control DNA can be tagged with biotin (Tizard et al. PNAS 87, 4514 (1990)) before heteroduplex formation or after heteroduplex formation and cleavage. Methods for the detection of biotinylated DNA after polyacrylamide gel electrophoresis have been disclosed (Ausubel et al. supra Chapter 7). In yet another alternative method, test or control DNA may be tagged with fluorescent dNTPs (i.e. fluorescein, see Ansorge, W., et al. Nucl. Acids Res. 15, 4593 (1987); Johnston-Dow, E., et al. BioTechniques 5, 754 (1987); Prober, J.. et al. Science 238, 336 (1987)) before heteroduplex formation or after heteroduplex formation and cleavage. In yet another example, the 3'→5' exonuclease activity of certain DNA polymerases, in particular T4 DNA polymerase, may be used to radiolabel heteroduplex DNA after cleavage. Cleaved DNA can be analyzed by denaturing polyacrylamide gel electrophoresis and autoradiography.

iv) Additional Detection Techniques:

a) gel techniques: In addition to the well known basic denaturing polyacrylamide gel electrophoresis technique described above (i.e. 4% to 8% polyacrylamide, 7M urea in a 40-cm long gel of uniform thickness see Sambrook et al. supra), a variety of electrophoretic methods are available for increasing the resolution of bacteriophage T4 endonuclease VII cleavage products and in particular, analyzing large cleavage products (ie. >2 kb). Denaturing polyacrylamide gels exhibiting increased resolution have the advantage of allowing a more precise determination of the specific site of mutation in a test DNA. Furthermore, such gels allow improved analysis of cleaved DNA. For example, wedge-shaped spacers may be used to create a field gradient or incorporate a buffer gradient, an electrolyte gradient, or an acrylamide step gradient. Formamide may be included in a standard denaturing polyacrylamide gel or longer gels may also be employed (80 to 100 cm). These electrophoretic techniques have been described in detail (Ausubel et al. supra Chapter 7). Cleavage products larger than 2 kb can be specifically cut with a restriction enzyme in order to decrease fragment size. Those art-skilled will understand that the choice of a particular restriction enzyme to specifically cut a large cleavage product will be governed by a restriction enzyme map of the particular DNA to be analyzed. Alternatively, a large cleavage product can be electrophoresed on a denaturing (i.e. alkaline) agarose gel and directly visualized by reagents (e.g. stains or dyes) which interact with DNA, for example silver, ethidium bromide, acridine orange, 4,6-diamidino-2-phenylindol (i.e. DAPI), Hoechst dyes and the like (see Sambrook et al. supra and Bassam, B. J. et al. Anal. Biochem. 196, 80 (1991) ), or the electrophoresed DNA can be transferred to a membrane, for example DEAE-cellulose, nylon, or other suitable membrane; the transferred and membrane-bound DNA being visualized by filter hybridization with a radioactive or non-radioactive (i.e. biotin, digoxigenin, fluorescein) tagged probe, followed by autoradiography, streptavidin-alkaline phosphatase, digoxygenin visualization techniques (see ClonTech Product Catalogue, 1989/1990; Boehringer Mannheim Catalog (1993)) or fluorescence detection.

ii) Anchoring heteroduplex DNA to a Solid Support: Hemi-biotinylated test or control DNA can be prepared by adding one 5' end biotin tagged oligonucleotide primer to a PCR amplification reaction. In such a PCR reaction, only one DNA strand includes a biotin tag at the 5' end. After PCR amplification, the test and control DNAs are denatured, either independently or together, annealed, and allowed to form heteroduplexes. The heteroduplexes are subsequently bound to a solid support. Preferred solid supports include avidin- or streptavidin-coated surfaces, for example, ovidin- or streptavidin-coated microtitre dishes, or streptavidin-coated ferromagnetic beads. Methods for anchoring hemibiotinylated DNA to magnetic beads have been described (Hultman, T. et al. BioTechniques 10, 84 (1991); Kaneoka, H. et al. BioTechniques 10, 30 (1991)). After obtaining a biotinylated heteroduplex anchored to a magnetic bead, the anchored heteroduplex is cleaved on both strands with a resolvase, preferably bacteriophage T4 endonuclease VII. After cleavage, newly exposed 5' ends are tagged with one or more detection moieties as described above, preferably biotin is used to tag newly exposed 5' ends, and the magnetic beads are concentrated by microfuge centrifugation. The supernatant or beads can be assayed for biotinylated (i.e. cleaved) DNA by gel electrophoresis (see above), or more conveniently by the use of streptavidin-alkaline phosphatase visualization techniques (Bethesda Research Laboratories Catalogue and Reference Guide, (1989); Clontech Catalog (1989/1990)).

In an alternative method, hemi-biotinylated DNA tagged at one 5' end with biotin can be tagged with an additional detection moiety at the other 5' end after binding to an avidin- or streptovidin-coated surface, preferably a fluorescent nucleotide (i.e. a fluorescein labelled nucleotide, see Clontech Catalog (1989/1990) is tagged to the other 5' end or a radioactive nucleotide is used to tag the other 5' end. After binding to a surface which includes avidin or streptavidin, followed by resolvase cleavage, preferably cleavage with bacteriophage T4 endonuclease VII, the supernatant can be analyzed for fluorescence or radioactivity.

In another alternative method, a DNA oligonucleotide primer for PCR can be tagged with a detection moiety such as digoxigenin. After amplification and duplex formation, tagged DNA is anchored to a surface bearing an antibody capable of binding digoxigenin (see Boehringer Mannheim Catalog (1993)). In yet another alternative method, DNA can be tagged with a detection moiety such as an oligo dT tail, and bound to a nylon support via ultraviolet light crosslinking of the oligo-dT tail to the nylon support. The unique nucleic acid sequence is held to the nylon support through the oligo-dT tail and is available for duplex formation. In each of these two methods, DNA can be further tagged at an unbound end with biotin, a fluorescent nucleotide, a radioactive nucleotide, then, after duplex formation, cleaved with a resolvase, preferably bacteriophage T4 endonuclease VII. After cleavage, released nucleic acid can be detected by appropriate methods described above.

Those skilled in the art will appreciate that a variety of methods exist for adding a detection moiety to DNA. For example, Clontech has disclosed amino modifiers, and thiol modifiers which could be used to tag DNA with biotin, FITC or other fluorophores (Clontech Catalog (1989/1990)).

What is claimed is:

1. A method for detecting in an isolated test nucleic acid one or more mutations diagnostic of a disease or condition, said isolated test nucleic acid being derived from a eukaryotic cell, and preferentially hybridizing to an isolated control nucleic acid, said method comprising:
   a) isolating or providing by denaturation a single-stranded test nucleic acid and a single-stranded control nucleic acid;
   b) annealing said single-stranded test nucleic acid to said single-stranded control nucleic acid, wherein said annealing is sufficient to form a duplex between said single-stranded test nucleic acid and said single-stranded control nucleic acid;
   c) contacting said duplex with a resolvase, wherein said resolvase is capable of recognizing and cleaving all eight types of mismatches and wherein said contacting is under conditions which permit said resolvase to cause one or more breaks in said duplex; and
   d) detecting said one or more breaks as an indication of the presence in said test nucleic acid of one or more mutations which are diagnostic of said disease or condition.

2. A method for detecting one or more mutations in an isolated test nucleic acid which is derived from a eukaryotic cell, a eubacterial cell, a bacterial cell, a mycobacterial cell, a bacteriophage, a DNA virus, or an RNA virus, and which preferentially hybridizes to an isolated control nucleic acid, said method comprising:
   a) generating by amplification said isolated test nucleic acid;
   b) denaturing said amplified test nucleic acid to provide a single-stranded test nucleic acid;
   c) isolating or providing by denaturation a single-stranded control nucleic acid;
   d) annealing said single-stranded test nucleic acid to said single-stranded control nucleic acid, wherein said annealing is sufficient to form a duplex between said single-stranded test nucleic acid and said single-stranded control nucleic acid;
   e) contacting said duplex with a resolvase, wherein said resolvase is capable of recognizing and cleaving all eight types of mismatches and wherein said contacting is under conditions which permit said resolvase to cause one or more breaks in said duplex; and
   f) detecting said one or more breaks as an indication of the presence in said test nucleic acid of one or more mutations in said test nucleic acid.

3. The method of claim 1 or 2, wherein said resolvase is a bacteriophage or a eukaryotic resolvase.

4. The method of claim 3, wherein said bacteriophage resolvase is either bacteriophage T4 Endonuclease VII or bacteriophage T7 Endonuclease I.

5. The method of claim 3, wherein said eukaryotic resolvase is isolated from *Saccharomyces cerevisiae*.

6. The method of claim 5, wherein said *Saccharomyces cerevisiae* resolvase is any one of Endo X1, Endo X2 or Endo X3.

7. The method of claim 1 or 2, wherein said control nucleic acid or DNA is isolated from any one of a eukaryotic cell, a eubacterial cell, a bacterial cell, a mycobacterial cell, a bacteriophage, a DNA virus, or an RNA virus.

8. The method of claim 7, wherein said RNA virus is a human T-cell leukemia virus or a human immunodeficiency virus.

9. The method of 7, wherein said DNA virus is from any one of the family Adenoviridae, Papovaviridae, or Herpetoviridae.

10. The method of claim 7, wherein said test or said control nucleic acid or DNA is isolated from any one of the β-globin, phenylalanine hydroxylase, $\alpha_1$-antitrypsin, 21-hydroxylase, pyruvate dehydrogenase E1α-subunit, dihydropteridine reductase, rhodopsin, β-amyloid, nerve growth factor, superoxide dismutase, retinoblastoma, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes gene of a eukaryotic cell.

11. The method of claim 7, wherein said test or said control nucleic acid or DNA is isolated from an oncogene or a tumor suppressor gene of a eukaryotic cell.

12. The method of claim 11, wherein said oncogene is any one of the abl, akt, crk, erb-A, erb-B, ets, fes/fps, fgr, fms, fos, jun, kit, mil/raf, mos, myb, myc, H-ras, K-ras, rel, ros, sea, sis, ski, src, or yes oncogenes.

13. The method of claim 11, wherein said tumor suppressor gene is any one of the p53, retinoblastoma, adenomatous polyposis coli, NF-1, NF-2, human non-polyposis coli, MLH-1, MTS1, or MSH-2 genes.

14. The method of claim 7, wherein said eubacterial cell is from any one of the order Spirochaetales, Kinetoplastida or Actinomycetales.

15. The method of claim 7, wherein said eubacterial cell is from any one of the family Treponemataceae, Trypanosomatidae, or Mycobacteriaceae.

16. The method of claim 15, wherein said eubacterial cell is from any one of the species *Mycobacterium tuberculosis*, *Borrelia burgdorferi*, *Treponema pallidum*, or *Trypanosoma cruzi*.

17. The method of claim 1 or 2, wherein prior to said contact with said resolvase, said control nucleic acid is tagged with at least one detection moiety.

18. The method of claim 17, wherein said detection moiety is any one of a radioactive nucleotide, biotin, digoxygenin, a luminescent agent, a dye, or an enzyme.

19. The method of claim 18, wherein said control DNA is tagged only at a 5' end.

20. The method of claim 1 or 2, wherein between said contact with said resolvase and said detection step, said duplex is post-digestion 5' end-labeled with at least one detection moiety.

21. The method of claim 20, wherein said heteroduplex comprises at least one of a radioactive nucleotide, biotin, a luminescent agent, or an enzyme.

22. The method of claim 1 or 2, wherein said test or said control nucleic acid or DNA is a restriction enzyme fragment.

23. The method of claim 1 or 2, wherein said test or said control nucleic acid or DNA is produced by PCR amplification.

24. The method of claim 1 or 2, wherein said test or said control nucleic acid or said DNA is produced by propagation in a eukaryotic cell, a eubacterial cell, a bacterial cell, or a phage.

25. The method of claim 1 or 2, wherein said duplex is bound to a solid support at one 5' end.

26. The method of claim 7, wherein said control DNA is isolated from a gene encoding a cell cycle control protein.

27. A method for detecting one or more mutations in an isolated test nucleic acid which is at least 100 nucleotides in length and which preferentially hybridizes to an isolated control nucleic acid, said method comprising:

a) generating by amplification said isolated test nucleic acid;

b) denaturing said amplified test nucleic acid to provide a single-stranded test nucleic acid;

c) isolating or providing by denaturation a single-stranded control nucleic acid;

d) annealing said single-stranded test nucleic acid to said single-stranded control nucleic acid, wherein said annealing is sufficient to form a duplex between said single-stranded test nucleic acid and said single-stranded control nucleic acid;

e) contacting said duplex with a resolvase, wherein said resolvase is capable of recognizing and cleaving all eight types of mismatches and wherein said contacting is under conditions which permit said resolvase to cause one or more breaks in said duplex; and f) detecting said one or more breaks as an indication of the presence of one or more mutations in said test nucleic acid.

28. A method for detecting in an isolated test nucleic acid one or more mutations diagnostic of a disease or condition, said isolated test nucleic acid being at least 100 nucleotides in length and preferentially hybridizing to an isolated control nucleic acid, said method comprising:

a) isolating or providing by denaturation a single-stranded test nucleic acid and a single-stranded control nucleic acid;

b) annealing said single-stranded test nucleic acid to said single-stranded control nucleic acid, wherein said annealing is sufficient to form a duplex between said single-stranded test nucleic acid and said single-stranded control nucleic acid;

c) contacting said duplex with a resolvase, wherein said resolvase is capable of recognizing and cleaving all eight types of mismatches and wherein said contacting is under conditions which permit said resolvase to cause one or more breaks in said duplex; and d) detecting said one or more breaks as an indication of the presence in said test nucleic acid of one or more mutations which are diagnostic of said disease or condition.

29. The method of claim 28 or 27, wherein said test or said control nucleic acid is isolated from any one of a eukaryotic cell, a eubacterial cell, a bacterial cell, a mycobacterial cell, a bacteriophage, a DNA virus, or an RNA virus.

30. The method of claim 28 or 27, wherein said resolvase is a bacteriophage or a eukaryotic resolvase.

31. The method of claim 30, wherein said bacteriophage resolvase is bacteriophage T4 Endonuclease VII.

32. The method of claim 28 or 27, wherein said test nucleic acid is between 150 and 5000 nucleotides in length.

33. The method of claim 29, wherein said RNA virus is a human T-cell leukemia virus or a human immunodeficiency virus.

34. The method of claim 29, wherein said DNA virus is from any one of the family Adenoviridae, Papovaviridae, or Herpetoviridae.

35. The method of claim 29, wherein said test or said control nucleic acid is isolated from any one of the β-globin, phenylalanine hydroxylase, α$_1$-antitrypsin, 21-hydroxylase, pyruvate dehydrogenase Elα-subunit, dihydropteridine reductase, rhodopsin, β-amyloid, nerve growth factor, superoxide dismutase, retinoblastoma, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes gene of a eukaryotic cell.

36. The method of claim 29, wherein said test or said control nucleic acid is isolated from an oncogene, a tumor suppressor gene, or a cell cycle control gene of a eukaryotic cell.

37. The method of claim 36, wherein said oncogene is any one of the abl, akt, crk, erb-A, erb-B, ets, fes/fps, fgr, fms, fos, jun, kit, mil/raf, mos, myb, myc, H-ras, K-ras, tel, ros, sea, sis, ski, src, or yes oncogenes.

38. The method of claim 36, wherein said tumor suppressor gene is any one of the p53, retinoblastoma, adenomatous polyposis coli, NF-1, NF-2, human non-polyposis coli, MLH-1, MTS1, or MSH-2 genes.

39. The method of claim 36, where said cell cycle control protein is p21, p27, or p16.

40. The method of claim 29, wherein said eubacterial cell is from any one of the order Spirochaetales, Kinetoplastida, or Actinomycetales.

41. The method of claim 29, wherein said eubacterial cell is from any one of the family Treponemataceae, Trypanosomatidae, or Mycobacteriaceae.

42. The method of claim 41, wherein said eubacterial cell is from any one of the species *Mycobacterium tuberculosis*, *Borrelia burgdorferi*, *Treponema pallidum*, or *Trypanosoma cruzi*.

43. The method of claim 28 or 27; wherein prior to said contact with said resolvase, said control nucleic acid is tagged with at least one detection moiety.

44. The method of claim 43, wherein said detection moiety is any one of a radioactive nucleotide, biotin, digoxygenin, a luminescent agent, a dye, or an enzyme.

45. The method of claim 43, wherein said control nucleic acid is tagged only at a 5' end.

46. The method of claim 28 or 27, wherein between said contact with said resolvase and said detection step, said duplex is post-digestion 5' end-labeled with at least one detection moiety.

47. The method of claim 46, wherein said duplex comprises at least one of a radioactive nucleotide, biotin, a luminescent agent, a fluorescent agent, or an enzyme.

48. The method of claim 28 or 27, wherein said control nucleic acid is a restriction enzyme fragment.

49. The method of claim 28 or 27, wherein said control nucleic acid is produced by PCR amplification.

50. The method of claim 1 or 2, wherein said resolvase is bacteriophage T4 Endonuclease VII.

51. The method of claim 26, wherein said cell cycle control protein is p21, p27, or p16.

52. A method for typing a pathogenic microorganism strain, said method comprising:

a) isolating or providing by denaturation a single-stranded test nucleic acid derived from said pathogenic microorganism strain;

b) annealing said single-stranded test nucleic acid to a second single-stranded nucleic acid having a known pathogenic microorganism sequence, wherein said annealing is sufficient to form a duplex between said single-stranded nucleic acids;

c) contacting said duplex with a resolvase, wherein said resolvase is capable of recognizing and cleaving all eight types of mismatches and wherein said contacting is under conditions which permit said resolvase to cause one or more breaks in said duplex; and d) detecting said one or more breaks as an indication of the presence in said test nucleic acid of one or more mismatches, said mismatches indicating a nucleic acid sequence in said pathogenic microorganism which differs from said known pathogenic microorganism sequence.

53. The method of claim 52, wherein said pathogenic microorganism is a bacterium.

54. The method of claim 52, wherein said pathogenic microorganism is a virus.

55. The method of claim 54, wherein said virus is a retrovirus.

56. The method of claim 55, wherein said virus is a human immunodeficiency virus.

57. The method of claim 55, wherein said virus is HIV-1, HIV-2, HTLV-I, or HTLV-II.

58. The method of claim 52, wherein said pathogenic microorganism is a DNA virus.

59. The method of claim 52, wherein said pathogenic microorganism is chosen from any one of the family Adenoviridae, Papovaviridae, Herpetoviridae, or Mycobacteriaceae.

60. The method of claim 52, wherein said pathogenic microorganism is chosen from any one of the order Spirochaetales, Kinetolplastida, or Actinomycetales.

61. The method of claim 52, wherein said pathogenic microorganism is chosen from any one of the genus Treponema, Borrelia, or Streptococcus.

62. The method of claim 52, wherein said pathogenic microorganism is chosen from any one of Trepanosoma cruzi or Mycobacterium tuberculosis.

63. The method of claim 52, wherein said pathogenic microorganism is pathogenic to a mammal.

64. The method of claim 63, wherein said mammal is a human.

65. The method of claim 52, wherein said resolvase is a bacteriophage or a eukaryotic resolvase.

66. The method of claim 65, wherein said bacteriophage resolvase is bacteriophage T4 Endonuclease VII.

67. The method of claim 52, wherein said test nucleic acid is between 150 and 5000 nucleotides in length.

68. The method of claim 52, wherein prior to said contact with said resolvase, said control nucleic acid is tagged with at least one detection moiety.

69. The method of claim 52, wherein said detection moiety is any one of a radioactive nucleotide, biotin, digoxygenin, a luminescent agent, a dye, or an enzyme.

70. The method of claim 52, wherein said control nucleic acid is tagged only at a 5' end.

71. The method of claim 52, wherein between said contact with said resolvase and said detection step, said duplex is post-digestion 5' end-labeled with at least one detection moiety.

72. The method of claim 52, wherein said duplex comprises at least one of a radioactive nucleotide, biotin, a luminescent agent, a fluorescent agent, or an enzyme.

73. The method of claim 52, wherein said control nucleic acid is a restriction enzyme fragment.

74. The method of claim 52, wherein said test nucleic acid or said control nucleic acid is produced by PCR amplification.

* * * * *